United States Patent [19]

Nowacki et al.

[11] Patent Number: 4,745,921

[45] Date of Patent: May 24, 1988

[54] PLEATED DIAPHRAGM FOR COUPLING KIDNEY STONE DISINTEGRATOR TO HUMAN BODY

[75] Inventors: Christopher Nowacki, Arlington Heights; Alfred G. Brisson, Kildeer; Exequiel Dela-Cruz, Arlington Heights, all of Ill.

[73] Assignee: Trutek Research, Inc., Lake Zurich, Ill.

[21] Appl. No.: 945,850

[22] Filed: Dec. 23, 1986

[51] Int. Cl.[4] ............................................. A61B 17/22
[52] U.S. Cl. .................................. 128/328; 128/24 A
[58] Field of Search ............... 128/328, 64, 24 A, 54, 128/55

[56] References Cited

U.S. PATENT DOCUMENTS

| | | | |
|---|---|---|---|
| 3,942,531 | 3/1976 | Hoff et al. | 128/328 |
| 3,970,076 | 7/1976 | Hepp et al. | 128/64 |
| 4,311,147 | 1/1982 | Häusler | 128/328 |
| 4,539,989 | 10/1985 | Forssmann et al. | 128/328 |
| 4,620,545 | 11/1986 | Shene et al. | 128/328 |
| 4,630,607 | 12/1986 | Duinker et al. | 128/328 |

FOREIGN PATENT DOCUMENTS

| | | | |
|---|---|---|---|
| 0131653 | 1/1985 | European Pat. Off. | 128/328 |
| 2913251 | 10/1980 | Fed. Rep. of Germany | 128/328 |
| 2045616 | 11/1980 | United Kingdom | 128/52 |
| 2140693 | 12/1984 | United Kingdom | 128/328 |

Primary Examiner—Edgar S. Burr
Assistant Examiner—Tonya Lamb
Attorney, Agent, or Firm—Robert M. Wolters

[57] ABSTRACT

An extracorporeal kidney stone disintegrator comprises an ellipsoidal reflector having an open end. A spark gap is positioned in said reflector at the first focus point thereof. A flexible cap closes the otherwise open end of said reflector, and a body of liquid fills said reflector and said cap. The cap is adapted for disposition against a human body having therein a concretion such as a kidney stone to be disintegrated. The reflector is positioned so that the concretion lies on the second focus point of the reflector. Generation of a spark across said spark gap causes generation of a shock wave focused on the concretion and coupled to the concretion by the body of liquid and the tissues of the body through the cap. The cap has an annular pleat enhancing flexibility of the cap.

9 Claims, 1 Drawing Sheet

U.S. Patent
May 24, 1988
4,745,921
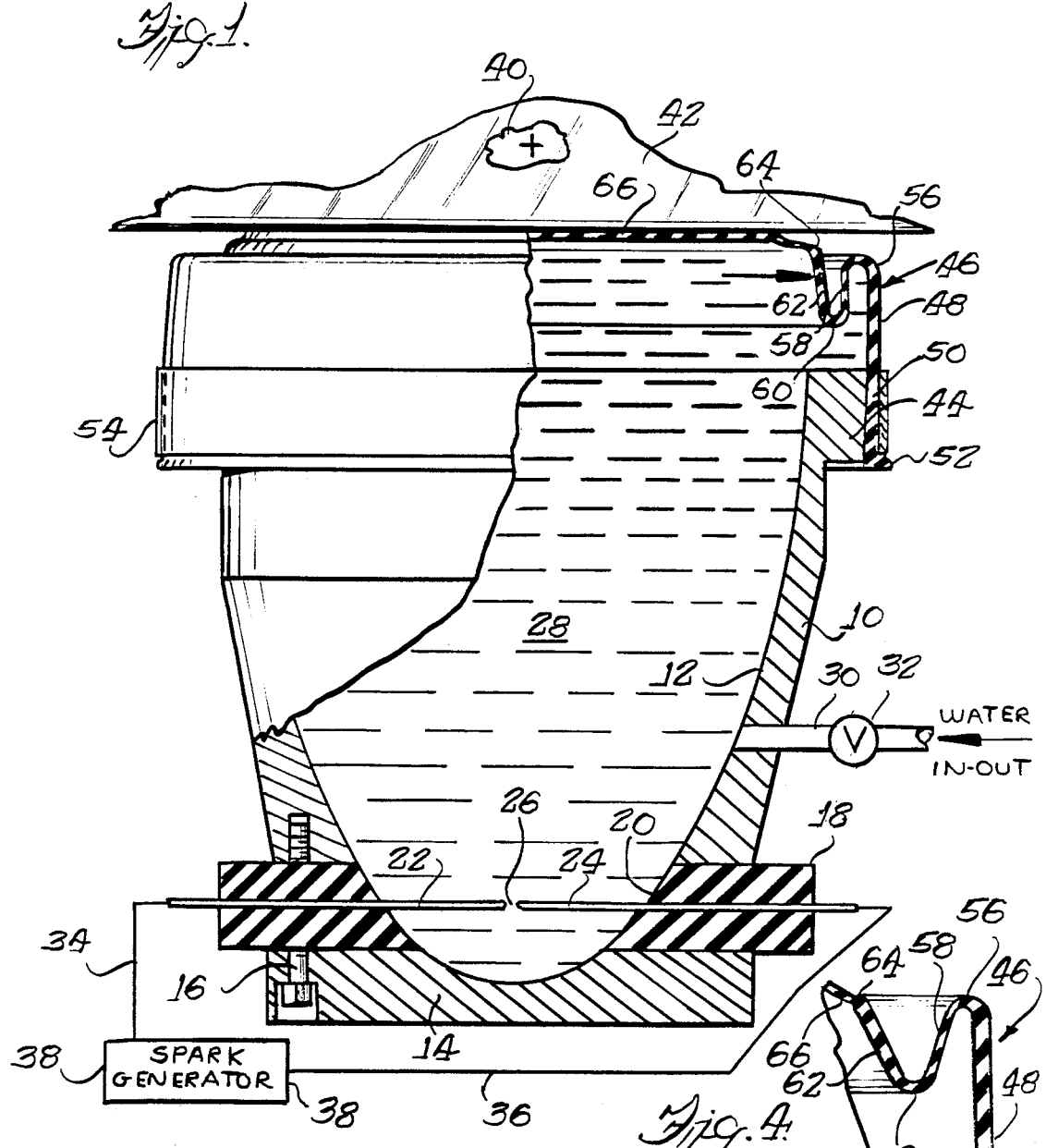
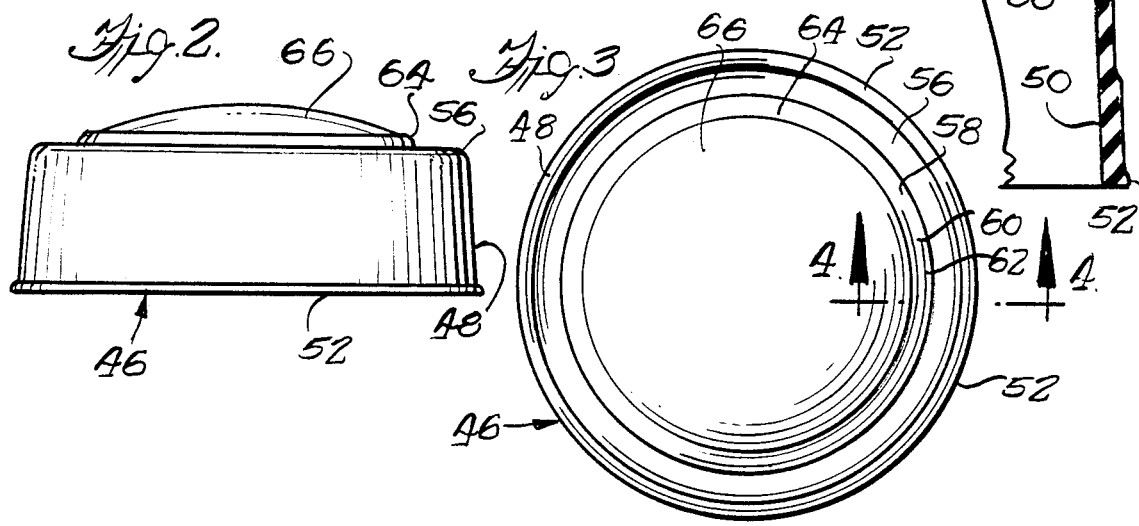

PLEATED DIAPHRAGM FOR COUPLING KIDNEY STONE DISINTEGRATOR TO HUMAN BODY

BACKGROUND OF THE INVENTION

Kidney stones, and also naturally occurring stones in the bladder and the ureter can be exquisitely painful, and often require surgical relief. Excision or destruction of stones in the bladder and sometimes in the ureter can be relatively easily accomplished, but removal of stones from the kidney is a major procedure.

Removal of stones from the kidney is a very serious and traumatic surgical procedure. A large incision is made in the body. The kidney is essentially removed from the body and cut open. The stone or stones are then removed, whereupon the kidney is sutured and returned to the body, with the body then being sutured. Various efforts have been made to destroy or disintegrate kidney stones so that they can be excreted with the urine.

Chemotherapy is available as a non-invasive therapy for uric acid stones. In this therapy, the urine is alkalyzed, and the stone is dissolved over a substantial period of time. This requires detection of the stone before an acute phase is reached.

The next step was the use of ultrasound or an electrohydraulic shock wave produced by discharging a capacitor across a spark gap under water or other suitable liquid. Early efforts required invasion of the body, either through the urethra or through a surgical incision.

Subsequently, efforts have been made for the extracorporeal destruction of kidney stones through the use of a focused shock wave. In U.S. Pat. No. 3,942,531, for example, a reflector is used which is a portion of an ellipsoid. The spark gap is located at the first focus point of the ellipsoid, and the ellipsoid is positioned relative to the body so that the kidney stone or other calculus or concretion is at the second focus point of the ellipsoid. The reflector is filled with water. Discharge of a spark across the gap causes rapid vaporization of a portion of the water, and resultant generation of a shock wave which is focused by the reflector on the kidney stone. The shock wave travels through the water in the ellipsoidal reflector, and through the human tissues to the kidney stone. A repetition of the spark gap shock wave generation over a period of perhaps an hour is necessary to destroy a kidney stone.

In accordance with U.S. Pat. No. 3,942,531, mentioned above, a flexible diaphragm is provided across the otherwise open end of the reflector to retain the water in the reflector, and to effect close contact with the skin of the patient, and thereby to effect efficient coupling of the shock wave through the water and through the tissues of the patient to the kidney stone to be destroyed.

In order that the kidney stone might be precisely in the second focus point of the ellipsoidal reflector, it is necessary that the reflector be moveable relative to the body of the patient, toward and away from the body, from side to side in two dimensions, and tilting.

OBJECTS AND SUMMARY OF THE PRESENT INVENTION

It is an object of the present invention to provide, in an extracorporeal kidney stone disintegrating apparatus having an electrohydraulic shock wave generator with an upwardly opening ellipsoidal reflector, a diaphragm or cap over the upper end which is configured and dimensioned for self-support and enhanced flexibility to facilitate positioning of the reflector relative to a human body having a kidney stone therein.

More particularly, it is an object of the present invention to provide a diaphragm or cap in accordance with the previous object wherein the cap is provided with an annular pleat, and wherein different areas of the cap are of different thicknesses to enhance strength and flexibility.

In accordance with the present invention an extracorporeal kidney stone disintegrator includes an electrohydraulic shock wave generator. The generator includes an upwardly opening truncated ellipsoidal reflector with a spark gap positioned at the first focus point of the ellipsoid. The reflector is positioned relative to a human body such that a kidney stone is positioned at the second focus point of the ellipsoid. The reflector is filled with water. Discharge of an electrical capacitor across the spark gap generates a spark which in turn generates an electrohydraulic shock wave. The shock wave is focused by the reflector and passes through the water and through the tissues of the human body to focus on the kidney stone. Repeated shock wave generation reduces the kidney stone to powder which passes out with the urine.

The otherwise open upper end of the reflector is closed by a diaphragm or cap to retain the water in the reflector and to effect efficient contact with the body of the patient having the kidney stone. The cap is provided with a peripheral pleat and various areas of the cap are of different thicknesses whereby the cap is simultaneously self-supporting and quite flexible so as to permit substantial movement of the reflector relative to the human body while maintaining contact of the water in the reflector with the body through the cap for highly efficient transfer of energy.

THE DRAWINGS

The present invention will be best understood from the following specification when taken in connection with the accompanying drawings wherein:

FIG. 1 is a side view partly in section showing an extracorporeal kidney stone disintegrator having the diaphragm or cap of the present invention;

FIG. 2 is a side view of the cap taken alone;

FIG. 3 is a top view of the cap; and

FIG. 4 is a fragmentary sectional view as taken substantially along the line 4—4 in FIG. 3.

DETAILED DESCRIPTION OF THE ILLUSTRATED EMBODIMENT

Apparatus for the extracorporeal disintegration of kidney stones includes a metal base or body 10 having an upwardly directed end opening ellipsoidal reflector 12 therein. The bottom 14 of the body 10 is a separate piece and is secured in place by a plurality of arcuately-spaced bolts 16 which also clamp an insulating ring 18 between the bottom 14 and the remainder of the body 10. The inner surface 20 of the ring comprises an annular concavity forming a continuation of the surface of the ellipsoidal reflector 12. The ring 18 supports a pair of diametrically opposed metallic rods 22 and 24 having the inner ends thereof in close proximity and defining a spark gap 26.

The reflector 12 is filled with water 28, and a pipe 30 is provided extending into the reflector through the body 10 and provided with a valve 32 for introducing water into the reflector 12 and for draining water therefrom. A separate drain may be provided if desired.

The rods 22 and 24 extend exteriorly of the ring 18, and the outer ends thereof are connected by wires 34 and 36 to a spark generator 38. As is known in the art, such a spark generator includes a large, high voltage capacitor and a charging voltage source. Discharge of the capacitor across the spark gap 26 causes rapid vaporization of water in the spark gap resulting in an electrohydraulic shock wave which is focused by the reflector to concentrate on the second focus point of the ellipsoidal reflector. As will be clear shortly hereinafter, the reflector is positioned so that the second focus point will lie on a kidney stone or the like concretion 40 in a human body 42.

The body 10 at its upper end has a circular peripheral flange 44 on which is mounted a cap or diaphragm 46. The cap or diaphragm is preferably made of a synthetic rubber such as neoprene, although silicone or other synthetic elastomers could be used. It is also contemplated that a plastic resin could be used. The material has a low coefficient of elasticity and is strong so that it does not absorb shock waves.

Relative thicknesses of material are important as well as shape, and actual dimensions of a satisfactory embodiment of the cap will be given hereinafter.

The cap includes a peripheral skirt 48 approximately 2.250 inches high and having a lower thickened portion 50, which is 0.750 inch high and having a wall thickness of 0.134 inch. The skirt is circular in outline and at its lower-most extremity has an internal diameter of 7.125 inches. An exterior peripheral bead 52 is formed on a lower portion 50 of the skirt 48. The skirt flares somewhat outwardly as it moves from top to bottom, and the thickened portion 50 surrounds the flange 44 on the body 10 and is clamped thereon by an encircling clamping band 54. Above the thickened portion 50 the skirt is somewhat thinner, being 0.125 inch in thickness. The thickness of the skirt is sufficient that it is vertically stiff, although somewhat yieldable laterally. However, lateral yieldability is resisted by the body of water 28 within the reflector that extends on up into the cap.

At the top of the skirt there is a fold bight or ridge 56 in which the wall thins to 0.093 inch. The bight has an inside radius of 0.125 inch, and at the inner margin of the bight there is a downwardly and inwardly extending wall 58 of 0.030 inch thickness. It will be observed that this wall is very substantially thinner than the skirt, and this imparts enhanced flexibility to the wall 58, which may also be considered as being a pleat. At the bottom of the wall or pleat 58 there is a bight or valley 60 having a wall thickness of 0.030 inch, the same as the pleat 58, and having an inside radius of 0.140 inch. The cap continues upwardly and inwardly as a frustoconical wall 62 from the inner margin of the bight 60, the wall 62 having a thickness of 0.060 inch. At the upper edge of the wall 62 there is a shoulder 64 having an inside radius of 0.140 inch, and having a transition in wall thickness from the 0.060 thickness of the wall 62 to a thickness of 0.010 inch. comprising a central closure or top wall 66. The top wall 66 tends to extend upwardly in a dome shape, as shown in FIG. 2, supported by the pressure of the water 28 in the reflector and in the cap. However, this top wall, being relatively very thin is quite flexible and readily conforms to the shape of the human body 42, and may be substantially flattened in FIG. 1, or may be formed to a nonflat, relatively complex shape determined by the contours of the human body against which it is pressed.

As has been noted heretofore, the skirt 48 is vertically rather stiff, and upstands readily, particularly as augmented by water inside the cap. The frustoconical wall 62 is sufficiently thick that it, considering its short height, is also relatively stiff in a vertical direction. On the other hand, the pleat 58 is relatively thin, and therefore is vertically rather readily deformable. The central portion or top wall 66, as previously noted, is quite flexible. Initial design considerations are such that the reflector will not have to be raised much farther relative to the human body than shown in FIG. 1. However, it may be necessary to lower the reflector, and in that case the diaphragm first bulges up somewhat as shown in FIG. 2. However, the diaphragm is capable of raising a great deal higher, and in this connection the wall or pleat 58 turns on itself in a more or less rolling action which allows the central portion or top wall 66 to rise quite extensively as may be needed. The pleat 58 is substantially 0.750 inch high, while the wall 62 is approximately 0.875 inch high. The bight 56 diametrically of the cap from center to center of the bight is 6.875 inches, while the same dimension on the bight 60 in relaxed, rest position is 6.0 inches. The diametrical distance across the shoulder 64 is 5.50 inches. The height of the shoulder 64 can be raised approximately 1.5 inches by complete inversion of the pleat 58 and straightening out of the bights 56 and 60. Additional height can be gained by doming of the top wall 66 as in FIG. 2. It is not anticipated that this much height will be needed, but it is available if the need should arise.

Dimensions of the various parts of the cap or diaphragm have been given, and the cap is a one-piece molding of elastomeric material, the material preferably being a synthetic elastomer such as neoprene or silicone rubber, although it is contemplated that the material could be a plastic resin material. The shock wave is coupled from the water 28 to the human body through the relatively thin top wall 66 with substantially no loss of energy. Coupling from the water to the tissues of the human body is highly efficient since the tissues are 80-85% water, whereby the energy is dissipated at the interface between the soft tissues and the hard kidney stone or other concretion. This results in breaking up of the kidney stone and reduction thereof to a powder which is excreted with the urine.

The term "kidney stone" is used herein for convenience, and is to be understood as including any concretion in the urinary tract whether it be in a kidney, the ureter, the bladder, or the urethra. Indeed, it is possible that the apparatus can be used on other parts of the body for treatment of tissues, such, for example, as cancer.

The specific example of the invention as herein shown and described is for illustrative purposes only. Various changes will no doubt occur to those skilled in the art, and will be understood as forming a part of the present invention insofar as they fall within the spirit and scope of the appended claims.

The invention is claimed as follows:

1. An extracorporeal kidney stone disintegrator comprising an ellipsoidal reflector having an axis of rotation and having an open end, means providing a spark gap in said reflector at the first focus point thereof, a flexible cap closing the otherwise open end of said reflector, and a body of liquid filling said reflector and said cap, said cap being adapted for disposition against a human body having therein a concretion such as a kidney stone to be disintegrated, the reflector being positioned so that the concretion lies on the second focus point of said reflector, generation of a spark gap across said spark gap causing generation of a shock wave focussed on said concretion and coupled to said concretion by said body of liquid and the tissues of said human body through said cap, said cap having an annular pleat enhancing flexibility of said cap, said cap including a central body contacting portion, a depending skirt mounted on said reflector, and said pleat being disposed between said central body contacting portion and said skirt, said central body contacting portion having a first predetermined thickness, said skirt having a second predetermined thickness greater than said first predetermined thickness, and said pleat having a thickness intermediate the thickness of said skirt and said central body contacting poriton.

2. A kidney stone disintegrator as set forth in claim 1 wherein said skirt has an upper edge and wherein said pleat comprises a depending outer pleat wall having a lower edge and an upper edge, said upper edge being joined to the upper edge of said skirt at an annular ridge, an inner upstanding pleat wall having a lower edge joined to said outer pleat wall at a valley at the respective lower edges of said inner and outer pleat walls, and said inner pleat wall having an upper edge joined to said central body contacting portion at a shoulder.

3. A kidney stone disintegrator as set forth in claim 2, said outer pleat wall being thicker than said central body contacting portion and thinner than said skirt, and said inner pleat wall being thicker than said outer pleat wall and thinner than said skirt.

4. A kidney stone disintegrator as set forth in claim 3, said outer pleat wall having a thickness on the order of three times said first predetermined thickness, said inner pleat wall having a thickness on the order of six times said first predetermined thickness, and said skirt having a thickness greater than ten times said first predetermined thickness.

5. A kidney stone disintegrator as set forth in claim 4 wherein said skirt has a thicker lower portion and an outstanding bead at the lower edge thereof, and a clamping band encircling said thicker lower portion above said bead and securing said skirt and said cap to said reflector.

6. A flexible, liquid-proof cap for use as in an electrohydraulic shock wave generator comprising a central body contacting portion adapted to conform to the contours of a human body, a depending skirt, and an annular pleat disposed between said central body contacting portion and said skirt enhancing flexibility of said cap, said central body contacting portion being of a predetermined thickness, said skirt being thicker than said central body contacting portion predetermined thickness, and said pleat being of a thickness intermediate the thicknesses of said central body contacting portion and said skirt, said pleat comprising a depending outer pleat wall having an upper edge and a lower edge, said skirt having an upper edge, the upper edge of said outer pleat wall being joined to the upper edge of said skirt at an annular ridge, and an inner upstanding pleat wall having a lower edge joined to said outer pleat wall lower edge at a valley, said inner pleat wall having an upper edge joined to said central body contacting portion at an annular shoulder.

7. A cap as set forth in claim 6 wherein said inner pleat wall being thicker than said outer pleat wall and thinner than said skirt.

8. A cap as set forth in claim 7 wherein said outer pleat wall is on the order of three times said predetermined thickness of said central body contacting portion, said inner pleat wall is on the order of six times said predetermined thickness, and the thickness of said skirt is more than ten times said predetermined thickness.

9. A cap as set forth in claim 8 wherein said skirt has a thicker lower portion and an outstanding bead at the lower edge thereof, said thicker portion being adapted to receive a clamping band to secure said cap to cooperating structure.

* * * * *